(12) United States Patent
Evron et al.

(10) Patent No.: US 7,778,685 B2
(45) Date of Patent: Aug. 17, 2010

(54) METHOD AND SYSTEM FOR POSITIONING A DEVICE IN A TUBULAR ORGAN

(75) Inventors: Rami Evron, Tel Aviv (IL); Ran Carmele, Rinatya (IL); Moshe Kleiman, Gedera (IL)

(73) Assignee: Paieon Inc., New York, NY (US)

( * ) Notice: Subject to any disclaimer, the term of this patent is extended or adjusted under 35 U.S.C. 154(b) by 710 days.

(21) Appl. No.: 10/451,543

(22) PCT Filed: Oct. 15, 2001

(86) PCT No.: PCT/IL01/00955

§ 371 (c)(1),
(2), (4) Date: Dec. 30, 2003

(87) PCT Pub. No.: WO02/36013

PCT Pub. Date: May 10, 2002

(65) Prior Publication Data

US 2004/0102697 A1 May 27, 2004

Related U.S. Application Data

(60) Provisional application No. 60/240,984, filed on Oct. 18, 2000.

(51) Int. Cl.
*A61B 5/05* (2006.01)
(52) U.S. Cl. .................. 600/424; 600/426; 600/429
(58) Field of Classification Search .......... 606/130; 600/424, 421, 42, 431, 433, 435
See application file for complete search history.

(56) References Cited

U.S. PATENT DOCUMENTS 4,263,916 A 4/1981 Brooks et al.

(Continued)

FOREIGN PATENT DOCUMENTS

DE 100 47 314 4/2001

(Continued)

OTHER PUBLICATIONS

Penney G P et al "A Comparison of Similarity Measures for Use in 2-D-3-D Medical Image Registration" IEEE Transactions on Medical Imaging, IEEE Service Center, Piscataway, NJ, US, vol. 17 ,No. 4. pp. 586-595.

(Continued)

*Primary Examiner*—Eric F Winakur
*Assistant Examiner*—Sanjay Cattungal
(74) *Attorney, Agent, or Firm*—Ohlandt, Greeley, Ruggiero & Perle, L.L.P.

(57) ABSTRACT

A system and method for positioning a device at a desired location in a tubular organ such as an artery. A three-dimensional reconstruction of the organ is obtained, and the desired location is marked in the reconstruction. The device is inserted into the organ and an image is obtained of the device and organ. The reconstruction with the marked location is projected onto a plane from the perspective of the image and the projection and image are superimposed. If the device is not at the desired location, the device is repositioned in the organ and an additional image of the device is obtained. The reconstruction is then projected onto a plane from the perspective of the additional image and the additional image and the projection are superimposed. This process is repeated, as required, until the device is in the desired location.

11 Claims, 4 Drawing Sheets

U.S. PATENT DOCUMENTS

| | | | |
|---|---|---|---|
| 4,889,128 A | | 12/1989 | Millar |
| 5,089,005 A | * | 2/1992 | Harada .................. 606/194 |
| 5,175,773 A | | 12/1992 | Garreau et al. |
| 5,203,777 A | | 4/1993 | Leeq |
| 5,207,226 A | | 5/1993 | Bailin et al. |
| 5,357,550 A | | 10/1994 | Asahina et al. |
| 5,446,800 A | | 8/1995 | Briggs et al. |
| 5,583,902 A | | 12/1996 | Bae |
| 5,699,799 A | | 12/1997 | Xu et al. |
| 5,718,724 A | | 2/1998 | Goicoechea et al. |
| 5,729,129 A | * | 3/1998 | Acker .................. 324/207.12 |
| 5,732,707 A | | 3/1998 | Widder et al. |
| 5,734,384 A | | 3/1998 | Yanof |
| 5,840,025 A | * | 11/1998 | Ben-Haim .................. 600/424 |
| 5,912,945 A | | 6/1999 | Da Silva et al. |
| 5,978,439 A | | 11/1999 | Koppe et al. |
| 6,027,460 A | | 2/2000 | Shturman |
| 6,047,080 A | | 4/2000 | Chen et al. |
| 6,094,591 A | | 7/2000 | Foltz et al. |
| 6,167,296 A | * | 12/2000 | Shahidi .................. 600/427 |
| 6,190,353 B1 | | 2/2001 | Makower et al. |
| 6,195,577 B1 | | 2/2001 | Truwit et al. |
| 6,231,518 B1 | * | 5/2001 | Grabek et al. .............. 600/508 |
| 6,233,476 B1 | * | 5/2001 | Strommer et al. .......... 600/424 |
| 6,246,898 B1 | | 6/2001 | Vesly et al. |
| 6,249,695 B1 | * | 6/2001 | Damadian .................. 600/427 |
| 6,290,673 B1 | | 9/2001 | Shanley |
| 6,301,498 B1 | | 10/2001 | Greenberg et al. |
| 6,317,621 B1 | | 11/2001 | Graumann et al. |
| 6,332,034 B1 | | 12/2001 | Makram-Ebeid et al. |
| 6,334,864 B1 | | 1/2002 | Amplatz et al. |
| 6,351,513 B1 | | 2/2002 | Bani-Hashemi et al. |
| 6,381,350 B1 | | 4/2002 | Klingensmith et al. |
| 6,381,483 B1 | * | 4/2002 | Hareyama et al. .......... 600/407 |
| 6,385,332 B1 | | 5/2002 | Zahalka et al. |
| 6,389,104 B1 | | 5/2002 | Beni-Hashemi et al. |
| 6,463,309 B1 | | 10/2002 | Ilia |
| 6,470,207 B1 | * | 10/2002 | Simon et al. .............. 600/426 |
| 6,501,848 B1 | | 12/2002 | Carroll et al. |
| 6,503,203 B1 | | 1/2003 | Rafter et al. |
| 6,505,064 B1 | | 1/2003 | Liu et al. |
| 6,535,756 B1 | | 3/2003 | Simon et al. |
| 6,544,178 B1 | * | 4/2003 | Grenon et al. ............. 600/443 |
| 6,544,230 B1 | | 4/2003 | Flaherty et al. |
| 6,669,635 B2 | * | 12/2003 | Kessman et al. ........... 600/437 |
| 6,709,444 B1 | | 3/2004 | Makower |
| 6,748,259 B1 | | 6/2004 | Benaron et al. |
| 6,990,368 B2 | * | 1/2006 | Simon et al. .............. 600/425 |
| 2002/0016544 A1 | * | 2/2002 | Hareyama et al. .......... 600/411 |
| 2002/0057825 A1 | | 5/2002 | Evron et al. |
| 2003/0032886 A1 | | 2/2003 | Dgany et al. |
| 2003/0199759 A1 | | 4/2003 | Richard |
| 2003/0208116 A1 | | 11/2003 | Liang et al. |
| 2004/0054248 A1 | | 3/2004 | Kimchy et al. ................ 600/3 |
| 2004/0102697 A1 | | 5/2004 | Evron |
| 2004/0136491 A1 | | 7/2004 | Iatrou et al. |
| 2005/0107688 A1 | * | 5/2005 | Strommer .................. 600/424 |
| 2005/0113686 A1 | | 5/2005 | Peckham |
| 2006/0036167 A1 | | 2/2006 | Shina |
| 2006/0058647 A1 | | 3/2006 | Strommer et al. ........... 600/434 |

FOREIGN PATENT DOCUMENTS

| | | |
|---|---|---|
| DE | 100 47 314 A1 | 4/2001 |
| EP | 0 885 594 | 12/1998 |
| EP | 1 005 835 | 6/2000 |
| EP | 1 005 835 A1 | 6/2000 |
| SU | 2 119 765 C1 | 10/1988 |
| WO | WO 96 25881 | 8/1996 |
| WO | WO 96/25881 | 8/1996 |
| WO | WO 99/13432 | 3/1999 |
| WO | WO 99 13432 | 3/1999 |
| WO | WO 01 58359 | 8/2001 |
| WO | WO 01/58359 | 8/2001 |
| WO | WO 01/85030 | 11/2001 |
| WO | WO 02/36013 | 5/2002 |
| WO | WO 02/36013 A1 | 5/2002 |
| WO | WO 03/096884 | 2/2004 |
| WO | WO 2005/008583 | 1/2005 |
| WO | WO 2005/020148 | 3/2005 |
| WO | WO 2005/031635 | 4/2005 |
| WO | WO 2006/033113 | 3/2006 |
| WO | WO 2006/061815 | 6/2006 |

OTHER PUBLICATIONS

Russakoff D B et al "Intensity-based 2D-3D spine image registration incorporating a single fiducial marker" Academic Radiology, Reston, VA, US, vol. 12, No. 1. pp. 37-50.

Srihari R et al "Image background search: combining object detection techniques with content-based image retrieval (CBIR) systems" Content-Based Access of Image and Video Libraries, 1999. (CBAIVL '99). Proceedings. IEEE Workshop on Fort Collins, CO, US, Los Alamitos, CA, USA,IEEE Comput. Soc, US, 1999, pp. 97-101.

Eiho S et al "Preoperative and intraoperative image processing for assisting endovascular stent grafting" Informatics Research For Development of Knowledge Society Infrastructure, 2004.ICKS 2004. International Conference on Kyoto, Japan Mar. 1-2, 2004, Piscataway, NJ, USA,IEEE. pp. 81-88.

Close R A et al "Accuracy Assessment of Layer Decomposition Using Simulated Angiographic Image Sequences" IEEE Transactions on Medical Imaging, IEEE Service Cente, Piscataway, NJ, US, vol. 20, No. 10. pp. 990-998.

Nelson T R et al "Three-dimensional ultrasound imaging" Ultrasound in Medicine and Biology, NewYork, NY, US, vol. 24, No. 9. pp. 1243-1270.

Bankman I "Handbook of Medical Imaging Progressing and Analysis" 2000, Academic Press, San Diego, London. pp. 359-374.

Garreau M et al. "A knowledge-based approach for 3-D reconstruction and labeling of vascular networks from biplane Angiographic projections" IEEE transactions on medical imaging, US, IEEE inc. vol. 10 , No. 2.

* cited by examiner

METHOD AND SYSTEM FOR POSITIONING A DEVICE IN A TUBULAR ORGAN

The present application claims the benefit of U.S. Provisional Appln. No. 60/240,984, filed Oct. 18, 2000.

FIELD OF THE INVENTION

The present invention relates to methods of positioning a device in a tubular organ of the body.

BACKGROUND OF TIRE INVENTION

Interventional radiology procedures are becoming increasingly important in the treatment of physiological abnormalities such as lumen stenosis or aneurysm. For example, in order to treat a stenotic coronary artery, it is often required to inflate a balloon, apply an atherectomy or thrombectomy device and place a stent (prosthesis) at a diseased artery site. The intravascular device (balloon, stent, atherectomy or thrombectomy device, for example) is usually mounted onto a guide wire and brought to the vessel to be treated using the guide wire and a catheter. When the catheter tip has reached the arterial region to be treated, the guide wire is extended from the catheter tip and is used to position the device inside the artery. Once the device is positioned within the artery and deployed, repositioning of the device is either impossible or may significantly increase the risk of injury to the artery and can result in total blockage to the treated artery.

Accurate positioning of the intravascular device at a specific site within an artery is essential for successful treatment. Improper positioning of a stent at the diseased site within the artery, or use of a longer stent than is actually required in order to compensate for inaccurate positioning, may significantly increase the chance for subsequent renarrowing of the artery. Moreover, in atherectomy procedures, inaccurate positioning and deployment of the device in the artery may cause a fatal thrombosis. Therefore, accurate determination of the location of an intravascular device in an artery is vital during any interventional therapeutic procedure.

The location of a catheter tip or intravascular device with reference to surrounding arterial anatomy is monitored by X-ray fluoroscopy. An angiographer releases a contrast material, such as iodine solution, from the catheter tip. The contrast material is carried from the catheter tip by the blood flow, and an X-ray image of the arterial anatomy in the vicinity of the catheter tip is obtained. Based upon the obtained X-ray image, the catheter is advanced until the desired arterial anatomy is reached. Then, the guide wire is extended from the catheter tip and brought to the diseased artery using fluoroscopy and short injections of contrast material. Usually, in order to treat the artery, the tip of the guide wire should pass through the diseased region to the distal end of the diseased region. Subsequently, an intravascular device is extended over the guide wire and brought to the diseased arterial region. Monitoring the location of the device inside the artery is performed by following the movement of two radio-opaque markers slidable along the guide wire that flank the device. The markers indicate the position of the device in reference to the guide wire in conjunction with short injections of contrast material. Typically, prior art methods require that the device be introduced stepwise into the organ and at each step the device and organ imaged so as to show the instantaneous position of the device relative to the organ. This is repeated as required until the device is positioned at the desired location. Such an approach requires that a contrast material be released into the organ in order for the organ to be imaged together with the device. Since many images may be required, the total amount of contrast material released into the blood may be quite large and harmful to the patient. Moreover, determining the location of the device in an artery in relation to the region to be treated is often inaccurate by this method. The main reason for this may be attributed to the fact that assessment of the morphology and length of disease in the artery is strongly dependent on the perspective from which the artery is viewed.

WO 96/25881 entitled "Method for ultrasound guidance during clinical procedures" published Aug. 29, 1996 describes a method using external ultrasound modality to derive angiography 3D reconstruction. External ultrasound modality cannot be applied for some organs, such as coronary arteries, which are an important implementation field for our invention.

Essentially, this reference describes a method for guiding a tool to reach an organ without intersecting other organs. It does not relate to navigation of a tool located inside a tubular organ to a pre-defined position within the tubular organ.

WO 01/58359 entitled "Ultrasonic Images" was published Aug. 16, 2001 i.e. after the international filing date of the present application and discloses an ultrasound imaging system that superimposes sectional views created from volumetric ultrasound data and the location data for an intervention device, such as a catheter. The position of an interventional medical device may be shown, in one or more views, relative to organs and tissues within a body as the interventional device is moved. The interventional device positional data is updated continuously and is superimposed on tissue images that may be updated less frequently, resulting in real-time or near real-time images of the interventional device relative to the tissues. The superimposed images permits medical personnel to perform procedures such as angiograms with minimal or no exposures of patients to x-rays and contrasting dye.

WO 99/13432 entitled "Apparatus and method for determining three-dimensional representations of tortuous vessels" published Mar. 18, 1999 discloses a method for three dimensional reconstruction of vessels. It does not teach how to use such a method to navigate a tool located side a tubular organ to a pre-defined position within the tubular organ.

It would therefore be desirable to provide a method and system for navigating a tool located inside a tubular organ to a predefined position within the tubular organ. It would be particularly advantageous to provide such a method and system where re-imaging of the organ for each incremental advance of the device in the organ is avoided.

SUMMARY OF THE INVENTION

The present invention provides a method and system for positioning a device located inside a tubular organ such as an artery, a blood vessel, or a urethra. The device encompasses, for example, intravascular devices, such as, catheters, balloons, stents, atherectomy and thrombectomy devices.

In accordance with the invention, positioning of the device in a tubular organ, such as an artery is performed utilizing a three-dimensional computer reconstruction of the organ. In the case of an artery, a three-dimensional reconstruction of the artery may be displayed on a monitor screen from any selected perspective. This allows a diseased artery, for example, to be viewed in the reconstruction from a perspective that is optimal for assessing the morphology and the length of disease in the artery. This in turn permits accurate determination of a location where an intravascular device should be deployed. A three-dimensional reconstruction of an artery may be obtained for example, as disclosed in Applicant's WO 01/85030 entitled "System and Method for Three- Dimensional Reconstruction of an Artery" published on Nov. 15, 2001. The reconstruction is displayed on a monitor screen, and the location where the device is to be deployed is determined and marked in the reconstruction taking into consideration the abnormality characteristics, the nominal dimensions of the device and its dimensions after deployment.

The device is mounted on a guide wire and is brought to the desired arterial region by a catheter, as is known in the art. Then, the guide wire is extended from the catheter tip and is used to navigate inside the arterial anatomy until the target artery has been reached.

In accordance with one embodiment of the invention, the device is inserted into the artery along the guide wire and an X-ray image of the artery, the guide wire and the device is obtained. The location of the device in the artery is determined by following the movement of two radio-opaque markers along the guide wire as the device moves along the guide wire. Then, a two-dimensional projection of the reconstruction, including the region marked for deployment, is obtained from the same perspective as the image, and superimposed onto the image. The superimposition thus shows simultaneously the device and the region of the artery marked in the reconstruction for deployment of the device. The device is advanced in the artery based upon a comparison of the present location of the device in the artery and the location of the marked region. A new image is then obtained of the device, and a superimposition of the reconstruction with the marked arterial region is obtained from the same perspective of the new image. Based upon a comparison of the new location of the device in the artery and the location of the marked region, the device is advanced towards the desired region. This process is repeated until the device appears in an image in the region of the artery marked in the reconstruction for deployment.

In accordance with another embodiment of the invention, two or more images of the artery are obtained and a three dimensional computer reconstruction of the artery is generated from the images. The location at which the device is to be deployed is then determined and marked in the reconstruction taking into consideration the abnormality characteristics, the nominal dimensions of the device and its dimensions after deployment. Contrast material is released from the catheter tip and an image of the artery to be treated and the device carried over a guide wire is obtained, preferably from the perspective of one of the images used to generate the computer reconstruction. The location of the device in the artery is determined by following the movement of two radio-opaque markers along the guide wire as the device moves along the guide wire. Then the position of the device in the is marked in the reconstruction and compared to the desired location as indicated in the reconstruction. If the device is at the desired location, then the process terminates. Otherwise, the device is advanced in the artery towards the desired location and a new fluoroscopic image of the device and the guide wire is then obtained from the same perspective without releasing contrast material from the catheter tip. The new location of the device in the artery is then determined from the position of the two radio-opaque markers and is then updated in the reconstruction. This process is repeated until the device is positioned in the desired location.

Thus, in one aspect the invention provides a method for positioning a device located inside a tubular organ, t a desired location inside the tubular organ, the method characterised by:
a) obtaining a three-dimensional reconstruction of the tubular organ;
b) marking in the reconstruction the desired location at which the device is to be located;
c) obtaining a two dimensional X-ray image of the intravascular device from a known perspective; and
d) using the three-dimensional reconstruction of the tubular organ in combination with the two-dimensional X-ray image of the device to position the device at said desired location inside the tubular organ.

The invention further provides a system for positioning an intravascular device located inside a tubular organ at a desired location in the tubular organ, the system comprising;
an X-ray imaging system for imaging the intravascular device from a known perspective so as to produce a two-dimensional X-ray image of the intravascular device,
a processor coupled to the X-ray imaging system and configured to project a three-dimensional reconstruction of the tubular organ on to a plane from said known perspective of the two-dimensional X-ray image of the intravascular device so as to form superimposition of either the three-dimensional reconstruction on to the two-dimensional X-ray image of the intravascular device or of the two-dimensional X-ray image of the intravascular device on to the three-dimensional reconstruction; and
a display displaying the superimposition.

The invention additionally provides a method for positioning a device located inside a tubular organ, at a desired location in the tubular organ, the method comprising:
a) generating a three-dimensional reconstruction of the tubular organ based upon first and second images of the tabular organ derived from respective first and second different perspectives;
b) marking the desired location in the reconstruction;
c) inserting the device into the tubular organ;
d) obtaining a composite image of the device and the tubular organ, the composite image being obtained from said first perspective;
e) computing and presenting in the reconstruction the location of the device in the tubular organ;
f) if the device is not located at the desired location, then:
   i) repositioning the device in the tubular organ;
   ii) obtaining an image of the device from said first perspective; and
   iii) repeating e) and f) as required until the device is located at the desired location.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF SPECIFIC EMBODIMENTS

Figure 1:
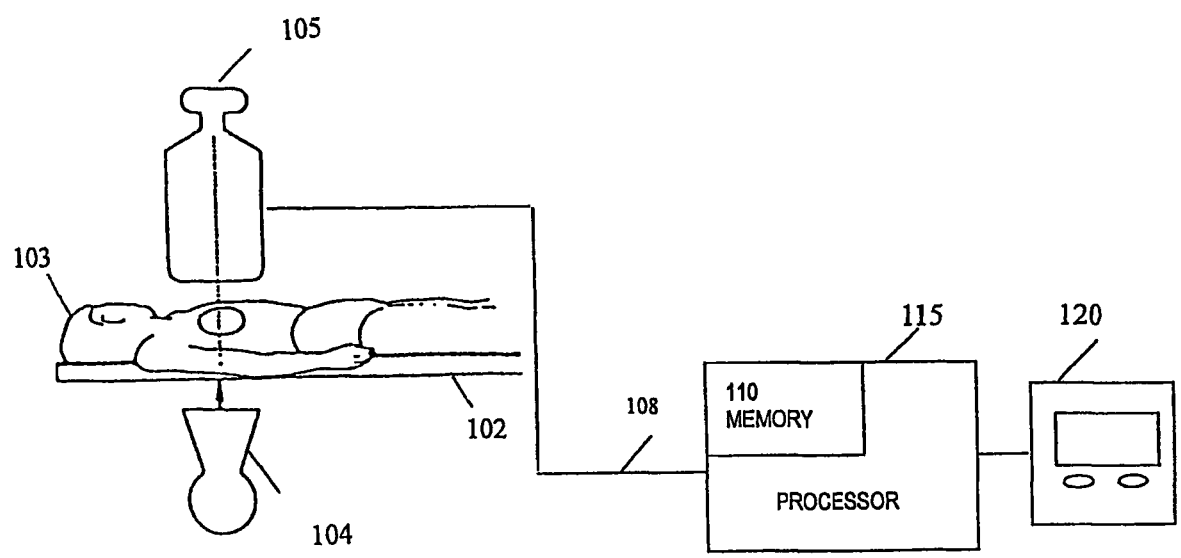
FIG. 1 shows a system for positioning a device in an artery according to one embodiment of the invention.

Referring first to FIG. 1, shown is a system for positioning a catheter or intravascular device at a desired location within an artery in accordance with one embodiment of the invention. The system comprises a table 102 upon which a patient 103 lies. An X-ray source 104 is located under the table 102 for projecting X-rays through the patient 103 to an X-rays camera 105 located above the table 102, diametrically opposite the X-rays source 104. The X-ray camera 105 generates video signals 108 representing one or more X-ray images of the patient 103. The video signals 108 are stored in a memory 110 of a processor 115. Images captured by the X-ray camera 105 may be viewed on a monitor 120 either in real-time or after being retrieved from the memory 110.

Figure 2:
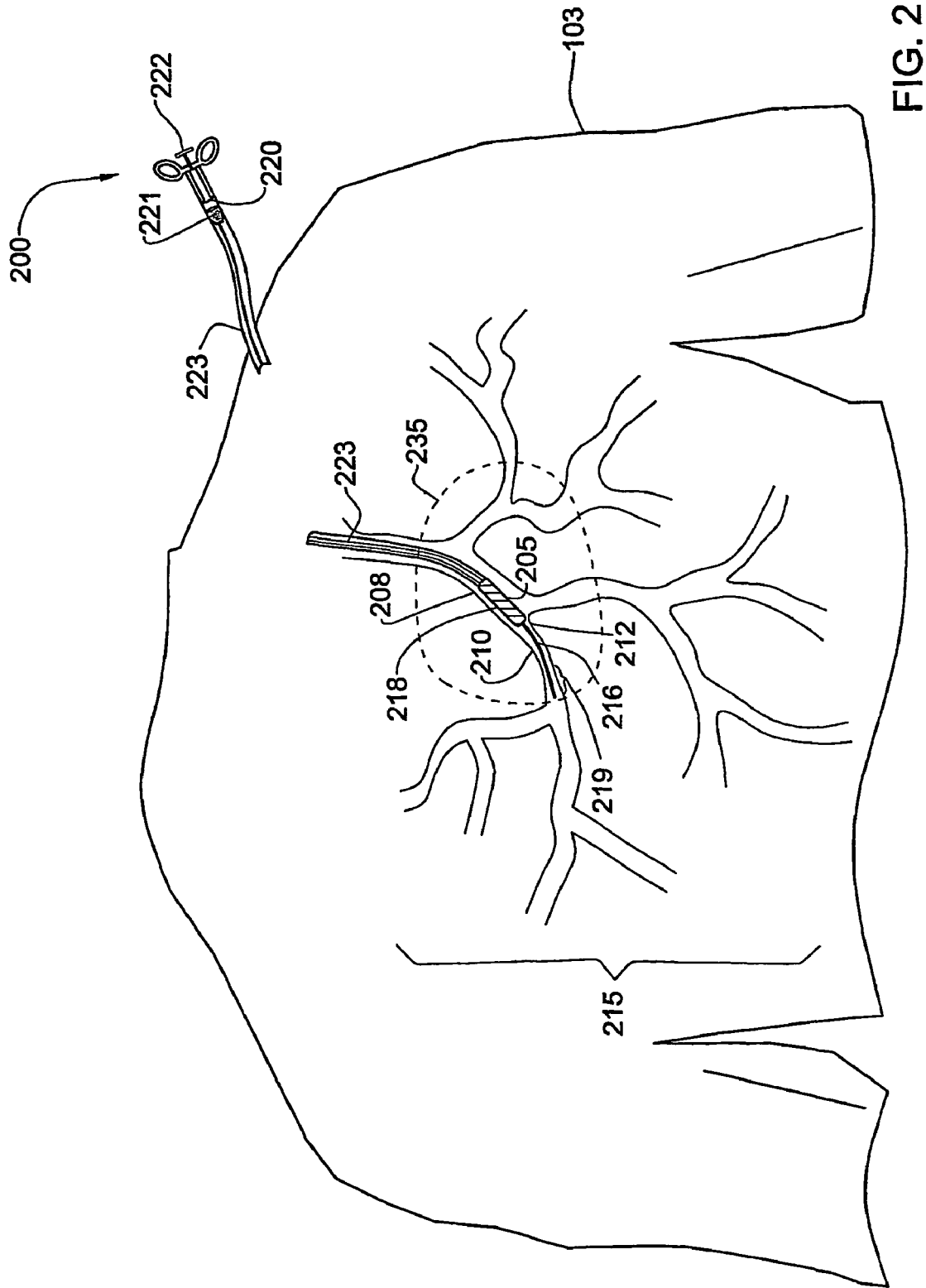
FIG. 2 shows a device being navigated through an arterial system.

FIG. 2 shows a catheter 200 the tip 205 of which bas been positioned at an aperture 212 of an artery 210 that is part of an arterial tree 215 of the patient 103. The catheter 200 may be used to deliver an intravascular device 218 mounted on a guide wire 216 to a desired location 219 within the artery 210. The catheter 200 is connected to a reservoir 220 containing a radio-opaque liquid 221 such as an iodine solution that is conducted from the reservoir 220 to the catheter tip 205 and released from the catheter tip 205 as required by depressing a piston 222. When contrast material 221 is released from the catheter tip 205, an image is obtained of the arterial tree in the vicinity 235 of the catheter tip 205 by the X-ray camera 105. Based upon the obtained image, the catheter tip is brought to the arterial system 215, which contains the artery to be treated 210. Then, the guide wire 216 is extended from the catheter tip 205 and brought to the diseased region within an artery 219 using fluoroscopy and short injections of contrast material. After positioning of the guide wire 216 within the artery 210, the device 218 is inserted into the artery 210 towards the desired region to be treated 219 along the guide wire 216.

Figure 3:
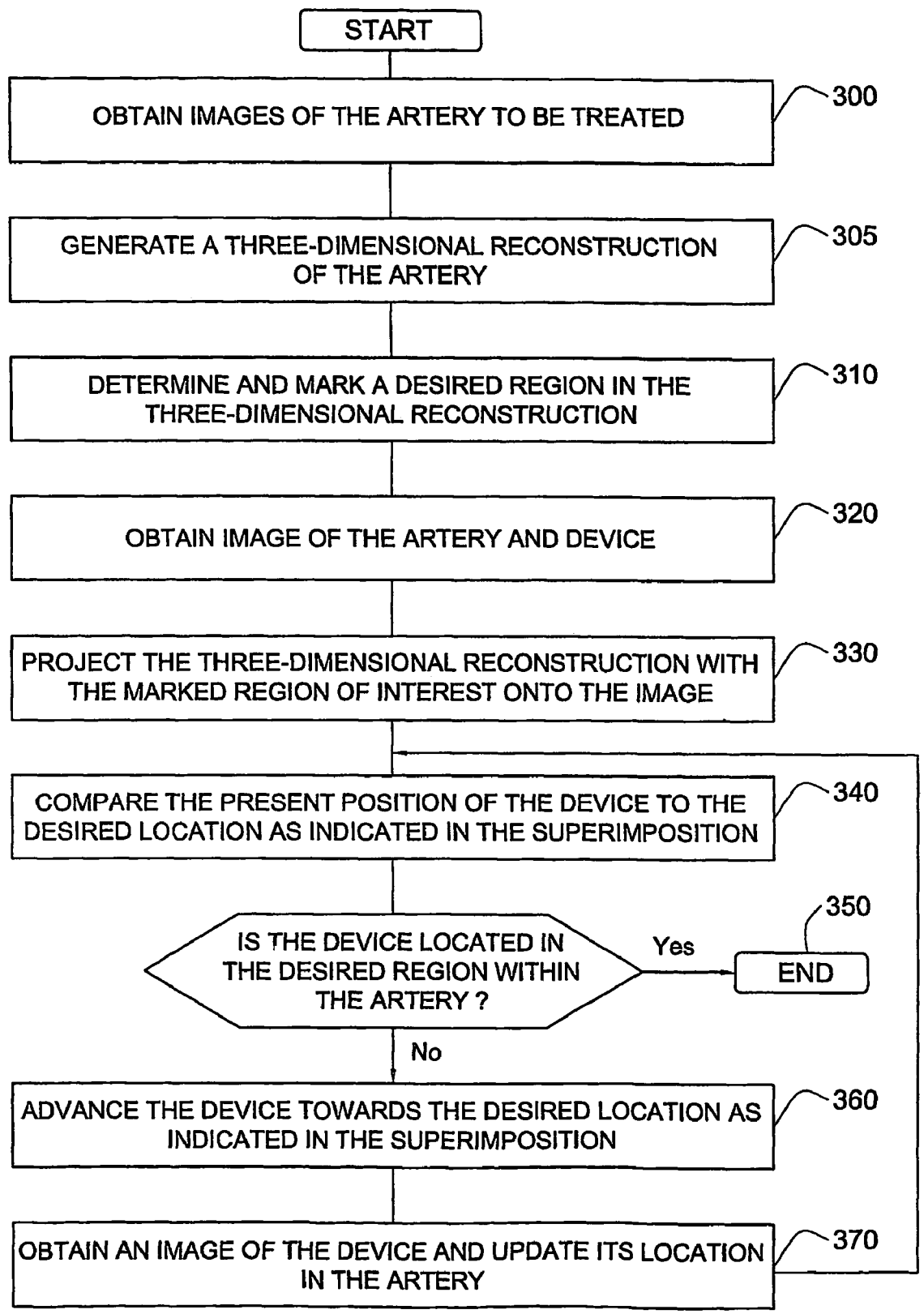
FIG. 3 shows a flow chart diagram for positioning a device in an artery in accordance with one embodiment of the invention.

FIG. 3 is a flow chart showing the principal steps for navigating the device 218 to the desired location 219 in accordance with one embodiment of the invention. In step 300, two or more images of the artery are obtained. Then, a three-dimensional computer reconstruction of the artery is generated from the images (step 305). Subsequently, taking into consideration the abnormality characteristics (for example, stenosis), the location where the device 218 is to be deployed is determined and marked in the reconstruction, and the nominal dimensions and its dimensions after deployment of the appropriate device are determined (step 310). In step 320, the contrast material 221 is released from the tip 205 of the catheter 200 and an image is obtained showing the position of the device 218 along the guide wire 216 as indicated by two radio-opaque markers flanking the device 218 on the guide wire, and the anatomy of the artery to be treated 208. In step 330, the reconstruction of the artery with the marked region of interest is projected onto a plane from the same perspective as the image, and superimposed onto the image. The superimposition thus shows simultaneously the device 218 and the region 210 of the artery marked in the reconstruction for deployment of the device. Then, the present position of the device 218 is compared to the desired location 219 as indicated in the superimposition (step 340). If the device 218 is at the desired location, then the process terminates (step 350). If no, the device 218 is advanced in the artery towards the desired location step 360). Then, a new image of the device 218 is obtained (step 370) and the process returns to step 340.

Figure 4:
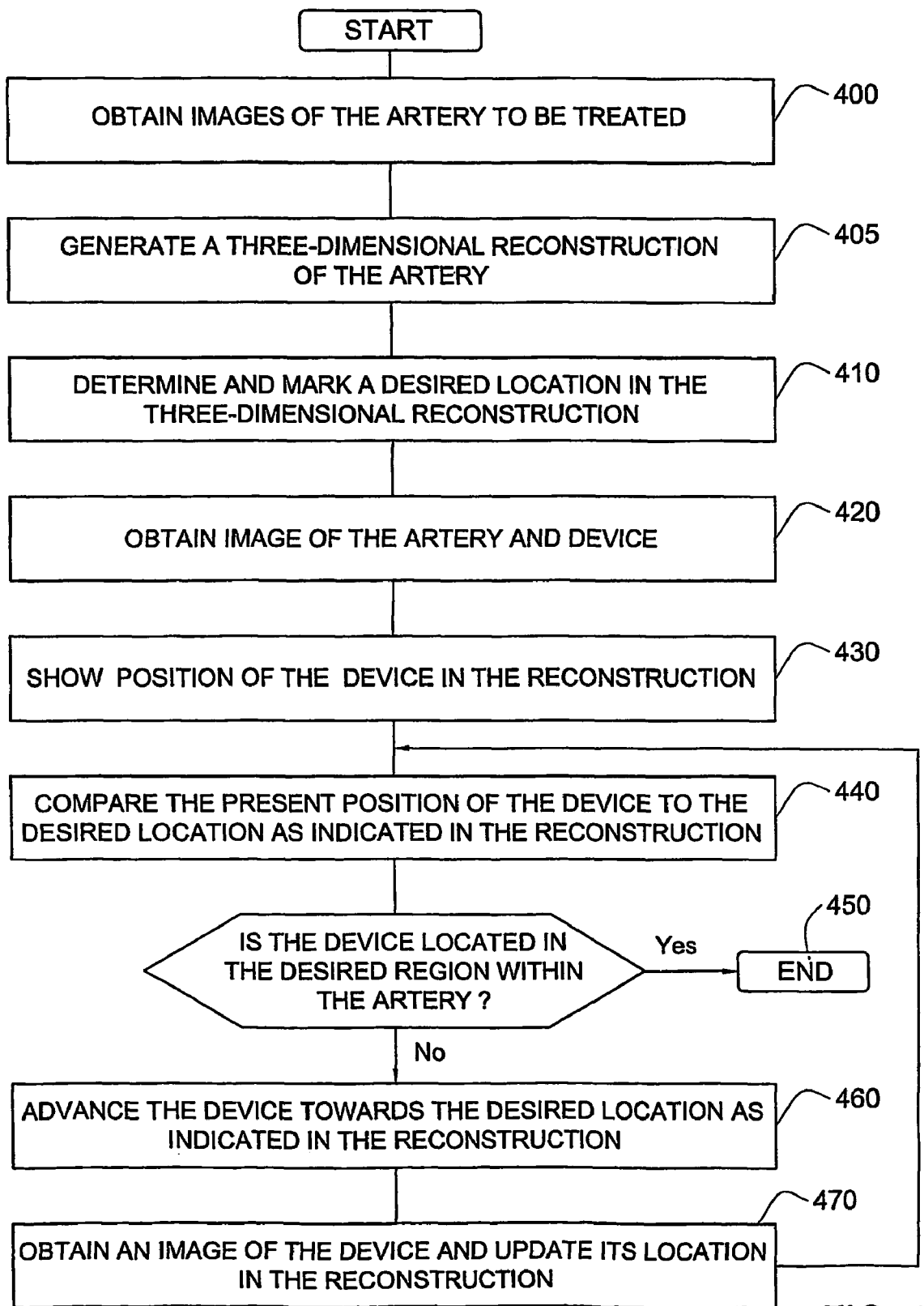
FIG. 4 shows a flow chart diagram for positioning a device in an artery in accordance with another embodiment of the invention.

FIG. 4 is a flow chart showing the principal steps for navigating the device 218 to a desired location within the artery 219 in accordance with another embodiment of the invention. In step 400, two or more images of the artery 210 are obtained. Then, a three-dimensional computer reconstruction of the artery is generated from the images (step 405). Then, the location at which the device is to be deployed is determined and marked in the reconstruction based upon the abnormality characteristics, the nominal dimensions of the device and its dimensions after deployment (step 410). In step 420, the contrast material 221 is released from the tip 205 of the catheter 200 and an image of the artery to be treated 208 and the device 218 carried over a guide wire 216 is obtained from the perspective of one of the images used to generate the computer reconstruction. In step 430, the position of the device in the artery is determined from the position of two radio-opaque markers flanking the device on the guide wire, and marked in the reconstruction. Then, the position of the device 218 is in the reconstruction is compared to the desired location 219 as indicated in the reconstruction (step 440). If the device 218 is at the desired location, then the process terminates (step 450). If not, the device 218 is advanced in the artery towards the desired location (460). A new fluoroscopic image of the device 218 and the guide 216 is then obtained from the same perspective without releasing contrast material from the catheter tip (step 470). The new location of the device in the artery is then in determined based upon following the two radio-opaque markers which represent its position along the guide wire and is then updated in the reconstruction and the process returns to step 440.

It will also be understood that the system according to the invention may be a suitably programmed computer. Likewise, the invention contemplates a computer program being readable by a computer for executing the method of the invention. The invention further contemplates a machine readable memory tangibly embodying a program of instructions executable by the machine for executing the method of the invention.

The invention claimed is:

1. A method for positioning an intravascular device located inside a tubular organ, at a desired location inside the tubular organ, the method characterised by:
 (a) obtaining a three-dimensional reconstruction of the tubular organ;
 (b) marking in the reconstruction the desired location at which the device is to be located;
 (c) obtaining a first two-dimensional X-ray image of the intravascular device located inside the tubular organ from a known perspective utilizing a processor that is responsive to respective positions of two radio-opaque markers flanking the intravascular device, the two-dimensional X-ray image taken after releasing contrast material;
 (d) obtaining a second two-dimensional X-ray image of the intravascular device located inside the tubular organ from the known perspective utilizing a processor that is responsive to respective positions of two radio-opaque markers flanking the intravascular device, the two-dimensional X-ray image taken without releasing contrast material; and
 (e) using the three-dimensional reconstruction of the tubular organ in combination with the first and second two-dimensional X-ray images of the device to position the device at said desired location inside the tubular organ.

2. The method according to claim 1, wherein step (e) includes:
 i) projecting the reconstruction of the tubular organ with the marked location on to a plane from the perspective of the image so as to form a projection and superimposing the projection on to the image;
 ii) if the device is not located at the desired location, then:
  1) repositioning a device inside the tubular organ;
  2) obtaining an additional image of the device without releasing contrast material; and 3) projecting the reconstruction of the tubular organ with the marked location on to a plane from the known perspective of the additional image and superimposing the projection on to the additional image;

iii) repeating step ii) as required until the device is located at the desired location.

3. The method according to claim 2, wherein step i) includes displaying a current location of the device on the three-dimensional reconstruction.

4. The method according to claim 1, wherein the tubular organ is an artery.

5. The method of claim 1 wherein the tubular organ is not visible in the second two-dimensional X-ray image.

6. A system for positioning an intravascular device located inside a tubular organ at a desired location in the tubular organ, the system comprising:

an X-ray imaging system for imaging the intravascular device from a known perspective so as to produce a first two-dimensional X-ray image of the intravascular device located inside the tubular organ, the first two-dimensional X-ray image taken after releasing contrast material, and a second two-dimensional X-ray image of the intravascular device located inside the tubular organ, the second two-dimensional X-ray image taken without releasing contrast material, a processor coupled to the X-ray imaging system and configured to project a three-dimensional reconstruction of the tubular organ on to a plane from said known perspective of the first and second two-dimensional X-ray image of the intravascular device so as to form superimposition of either the three-dimensional reconstruction on to the first and second two-dimensional X-ray image of the intravascular device, or of the first and second two-dimensional X-ray image of the intravascular device on to the three-dimensional reconstruction, wherein the processor is configured to mark the desired location of the intravascular device on the three-dimensional reconstruction; and a display displaying the superimposition, wherein the processor is responsive to respective positions of two radio-opaque markers flanking the intravascular device for determining the position of the intravascular device in the tubular organ so as to allow the intravascular device to be superimposed on to the three dimensional construction.

7. The system according to claim 6, wherein the processor is configured to compare a present position of the intravascular device to a desired location thereof indicated on the superimposition and to indicate a deviation between said present position and the desired location.

8. The system according to claim 7, wherein the processor is configured to mark the desired location of the intravascular device on the two-dimensional X-ray image of the intravascular device.

9. The method of claim 6 wherein tubular organ is not visible in the second two-dimensional X-ray image.

10. A method for positioning an intravascular device located inside a tubular organ, at a desired location inside the tubular organ, the method characterized by:

(a) obtaining a three-dimensional reconstruction of the tubular organ;

(b) marking in the reconstruction the desired location at which the device is to be located;

(c) obtaining a first two-dimensional X-ray image of the intravascular device located inside the tubular organ from a known perspective utilizing a processor that is responsive to respective positions of two radio-opaque markers flanking the intravascular device, wherein the tubular organ is visible in the first two-dimensional X-ray image;

(d) obtaining a second two-dimensional X-ray image of the intravascular device located inside the tubular organ from the known perspective utilizing a processor that is responsive to respective positions of two radio-opaque markers flanking the intravascular device, wherein the tubular organ is not visible in the second two-dimensional X-ray image; and (e) using the three-dimensional reconstruction of the tubular organ in combination with the first and second two-dimensional X-ray image of the device to position the device at said desired location inside the tubular organ.

11. The method of claim 10 wherein the second two-dimensional X-ray image is taken without the presence of contrast material within the tubular organ.

* * * * *